(12) United States Patent
Ray et al.

(10) Patent No.: US 9,913,576 B2
(45) Date of Patent: Mar. 13, 2018

(54) LAPAROSCOPE

(71) Applicants: Neil Anjon Ray, Durham, NC (US); Nasim Barzanian, Berkeley, CA (US); Jeffrey Yang, Berkeley, CA (US); Sakthivel Nagaraj, Berkeley, CA (US)

(72) Inventors: Neil Anjon Ray, Durham, NC (US); Nasim Barzanian, Berkeley, CA (US); Jeffrey Yang, Berkeley, CA (US); Sakthivel Nagaraj, Berkeley, CA (US)

( * ) Notice: Subject to any disclaimer, the term of this patent is extended or adjusted under 35 U.S.C. 154(b) by 232 days.

(21) Appl. No.: 14/611,766

(22) Filed: Feb. 2, 2015

(65) Prior Publication Data
US 2015/0216402 A1    Aug. 6, 2015

Related U.S. Application Data

(60) Provisional application No. 61/934,782, filed on Feb. 2, 2014.

(51) Int. Cl.
*A61B 1/00* (2006.01)
*A61B 1/12* (2006.01)
*A61B 1/313* (2006.01)
*G02B 27/00* (2006.01)

(52) U.S. Cl.
CPC ........ *A61B 1/126* (2013.01); *A61B 1/00096* (2013.01); *A61B 1/3132* (2013.01); *G02B 27/0006* (2013.01)

(58) Field of Classification Search
CPC ..... A61B 1/126; A61B 1/042; A61B 1/00096; A61B 1/3132; A61B 1/00163
See application file for complete search history.

(56) References Cited

U.S. PATENT DOCUMENTS

| | | | |
|---|---|---|---|
| 3,145,249 A * | 8/1964 | Meltzer | A61B 1/0008 15/250.1 |
| 5,176,630 A | 1/1993 | Shilling et al. | |
| 5,311,859 A | 5/1994 | Monroe et al. | |
| 5,807,239 A | 9/1998 | DiBernardo | |
| 6,855,107 B2 | 2/2005 | Avni et al. | |
| 2010/0174144 A1* | 7/2010 | Hsu | A61B 1/00087 600/122 |
| 2012/0035416 A1* | 2/2012 | Fernandez | A61B 1/05 600/102 |

* cited by examiner

*Primary Examiner* — Timothy J Neal
(74) *Attorney, Agent, or Firm* — Michael G. Johnston; Moore & Van Allen PLLC (57) ABSTRACT

A laparoscope comprises an elongated insertion tube having an open distal end. Optical means are provided for conducting an optical image of a target. The optical means includes an objective lens. A transparent sphere houses the lens. The sphere is rotatably disposed in the distal end of the tube such that a portion of the sphere protrudes from the tube. A ring-shaped wiper is fixed to the distal end of the tube for circumferentially engaging the sphere. Means are disposed in the tube for rotating the sphere, wherein the wiper removes debris and fluids from the surface of the sphere as the sphere rotates.

5 Claims, 7 Drawing Sheets

LAPAROSCOPE

CROSS REFERENCES

This application is related to U.S. provisional application No. 61/934,782, filed Feb. 2, 2014, entitled "ROTATIONALLY SELF-CLEANING SURGICAL CAMERA", naming Neil Anjon Ray, Nasim Barzanian, Jeffrey Yang, and Sakthivel Najaraj as the inventors. The contents of the provisional application are incorporated herein by reference in their entirety, and the benefit of the filing date of the provisional application is hereby claimed for all purposes that are legally served by such claim for the benefit of the filing date.

BACKGROUND

A laparoscope is described and, more particularly, a laparoscope which is self-cleaning for maintaining a viewing field during use.

Figure 11:
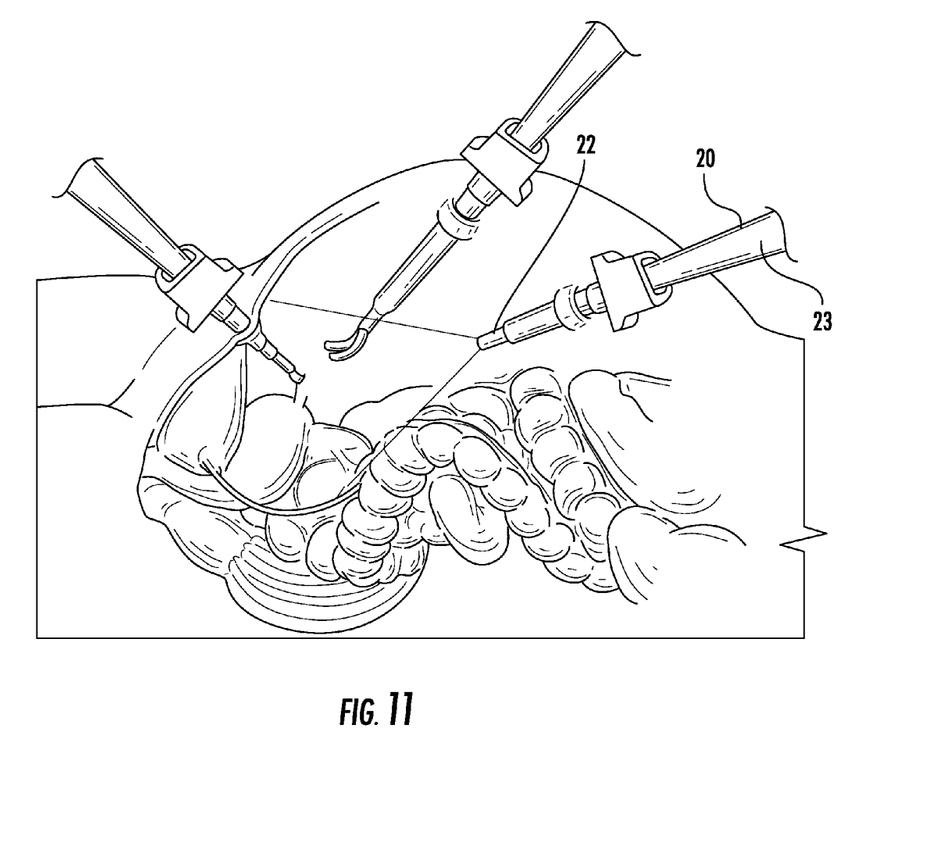
FIG. 11 is a schematic view of laparoscopic abdominal surgery using a laparoscope.

Laparoscopic surgery is a minimally invasive surgical technique performed in the abdomen through multiple small incisions. One of the surgical tools used is a laparoscope. The laparoscope is an imaging device comprising a lens tube which acquires an image of a target area in an objective lens at its distal end and a relay lens system within the lens tube. The laparoscope conventionally includes a camera which produces a video image of the target area, such as tissue within the body cavity of a patient, for display on a video monitor. In one application, a laparoscope is inserted through a transcutaneous trocar in a small incision and provides visualization while performing surgery in the abdominal cavity (FIG. 11).

One of the main problems with laparoscopic surgery is the issue of visibility of the surgical area through the lens. Visibility is reduced due to fogging, abdominal bleeding, and tissue smearing. Fogging of the laparoscope occurs because there is a difference in room temperature and abdominal temperature, causing condensation on the distal lens. Abdominal bleeding can occur as a result of the surgical procedure and can obscure vision when blood covers the lens. Finally, tissue inside of the trocar can smear the lens upon insertion of the laparoscope.

The physician typically removes the laparoscope from the patient for cleaning the lens and reinsertion into the abdomen. However, removal and reinsertion interrupts the flow of surgery and is time consuming, which can increase patient complications and medical expenses and lead to bacterial issues. Further, the path from the trocar entry to the site of surgery is cluttered and can leave debris on the lens.

Internal cleaning devices are available, but can readily become misplaced inside the patient if broken and some have only a limited number of uses before requiring replacement.

A mechanical solution utilizes carbon dioxide to create an air curtain near the tip of the lens, which prevents any debris from entering. Debris that passes through the air curtain can be cleaned either manually or through a built-in saline wash. However, this solution increases the bulk of the instrument and requires the use of larger unconventional incisions.

For the foregoing reasons, there is a need for keeping the view of the laparoscope uninhibited during surgery. Ideally, the laparoscope is fog-resistant, shielded from splashes, and otherwise remains clean in the body throughout surgery.

SUMMARY

A laparoscope comprises an elongated insertion tube having an open distal end. Optical means are provided for conducting an optical image of a target. The optical means includes an objective lens. A transparent sphere houses the lens. The sphere is rotatably disposed in the distal end of the tube such that a portion of the sphere protrudes from the tube. A ring-shaped wiper is fixed to the distal end of the tube for circumferentially engaging the sphere. Means are disposed in the tube for rotating the sphere, wherein the wiper removes debris and fluids from the surface of the sphere as the sphere rotates.

BRIEF DESCRIPTION OF THE DRAWINGS

For a more complete understanding of the laparoscope, reference should now be had to the embodiments shown in the accompanying drawings and described below. In the drawings:

FIG. 3 is a side elevation view of the distal portion of the laparoscope as shown in

FIG. 2.

DESCRIPTION

Certain terminology is used herein for convenience only and is not to be taken as a limitation on the invention. For example, words such as "upper," "lower," "left," "right," "horizontal," "vertical," "upward," and "downward" merely describe the configuration shown in the FIGs. Indeed, the components may be oriented in any direction and the terminology, therefore, should be understood as encompassing such variations unless specified otherwise.

Figure 1:
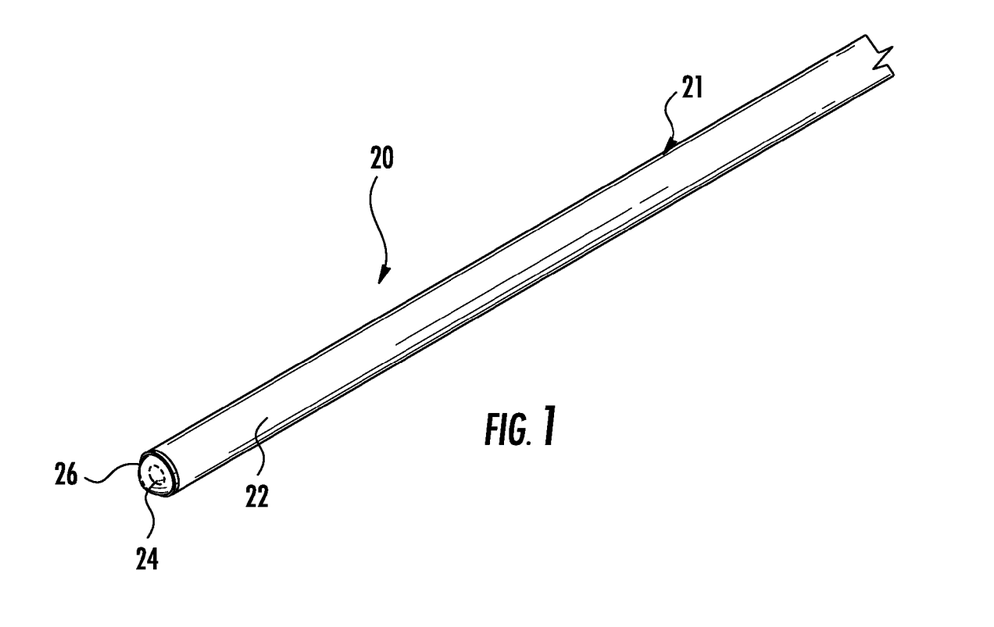
FIG. 1 is a perspective view of an embodiment of a laparoscope.

Referring now to the drawings, wherein like reference numerals designate corresponding or similar elements throughout the several views, an embodiment of a laparoscope assembly is shown in FIG. 1 and generally designated at 20. The laparoscope 20 has a body 21 which is sufficiently long so that a physician can comfortably direct the laparoscope ex-vivo. In one embodiment, the body 21 of the laparoscope 20 may be about 450 mm long, which is a conventional length. The laparoscope 20 comprises at a distal end an elongated rigid lens tube 22. The lens tube 22 is configured to pass through conventional surgical ports such as a trocar 23 (FIG. 11). The lens tube 22 houses an objective lens 24 at an open distal end of the lens tube 22. The lens 24 is disposed inside a hollow, transparent glass sphere 26 which partially protrudes from the distal end of the lens tube 22. The lens 24 may be a conventional optical lens that is utilized in current surgical cameras, including a flat lens or negative meniscus. Video signals may be supplied to an associated video monitor 38 at a proximal end of the body 21, for example, a color or black-and-white CRT, a flat-screen monitor, a projection monitor, or other viewing device.

The lens tube 22 may be made of stainless steel or of any other metal suitable for surgical devices. The sphere 26 may be formed from sapphire glass or of any other glass material having a low refractive index and which can be fashioned into a hollow sphere.

Figure 2:
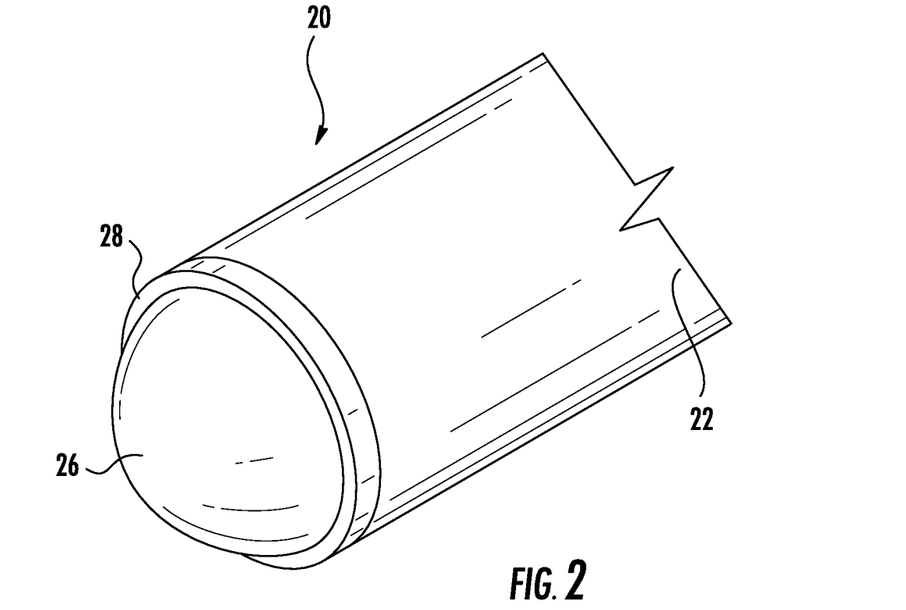
FIG. 2 is a perspective view of a distal portion of the laparoscope.
Figure 3:
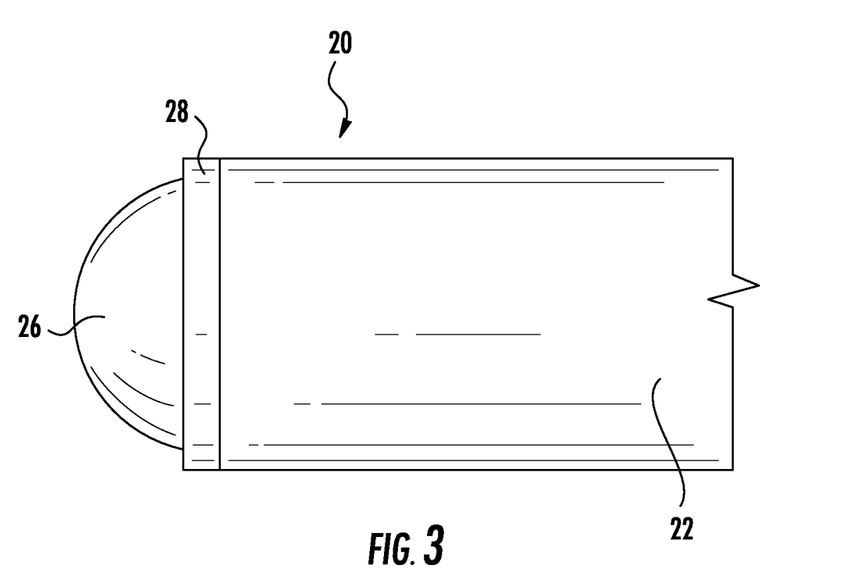
Figure 4:
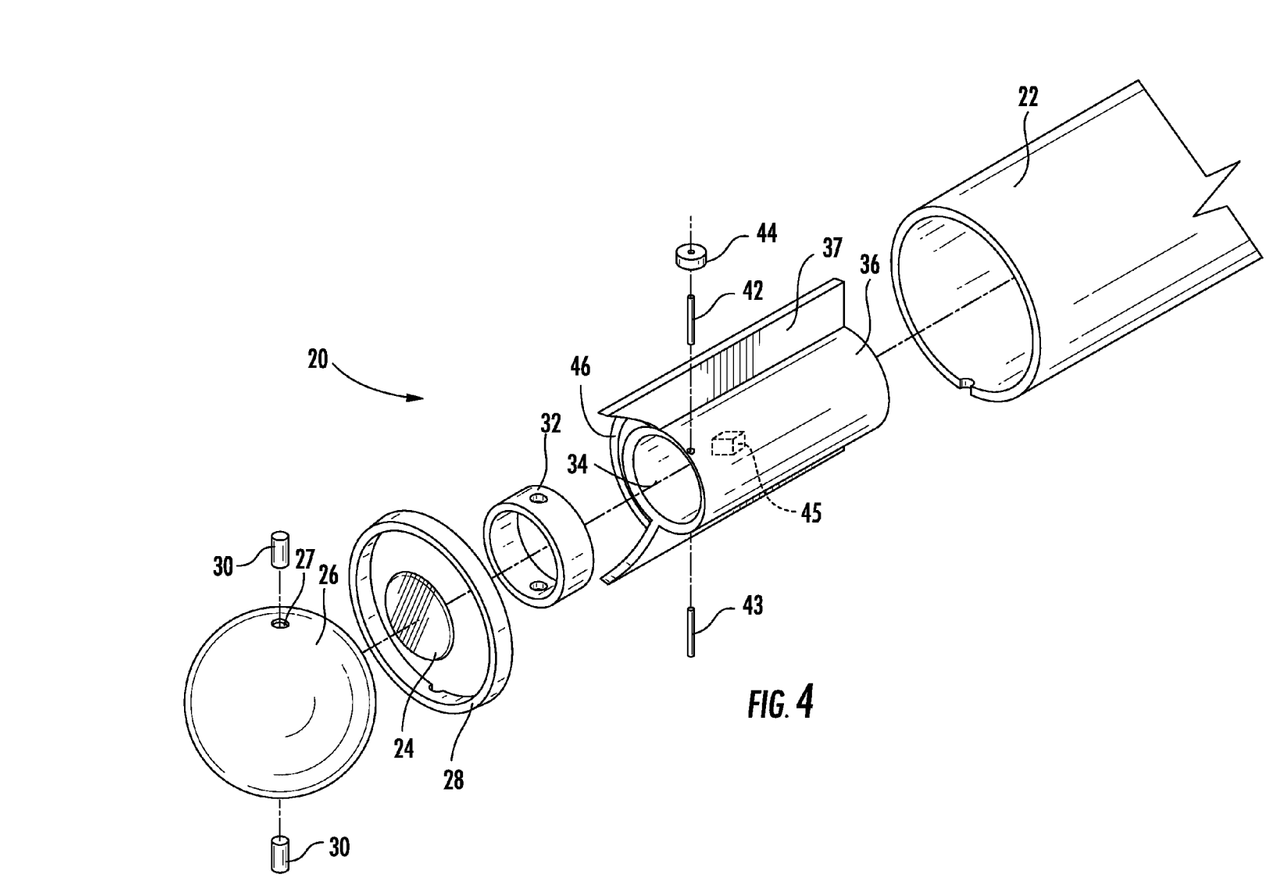
FIG. 4 is an exploded perspective view of the distal portion of the laparoscope as shown in FIG. 2.
Figure 5:
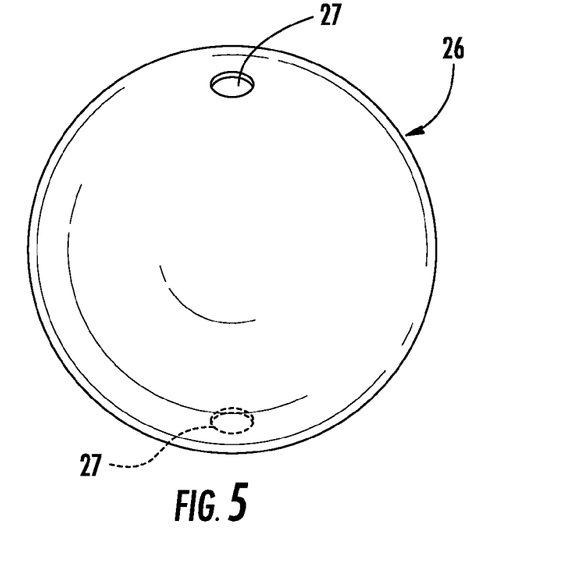
FIG. 5 is a perspective view of a transparent sphere for use in the laparoscope as shown in FIG. 1.
Figure 6:
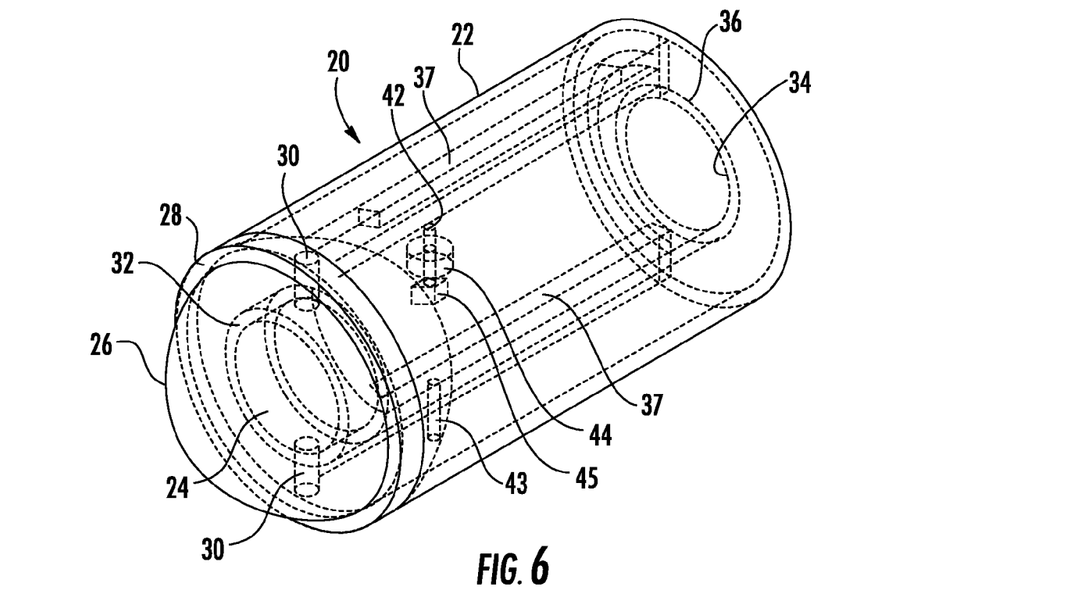
FIG. 6 is a perspective view of the distal portion of the laparoscope as shown in FIG. 2 with the internal components shown in phantom.
Figure 7:
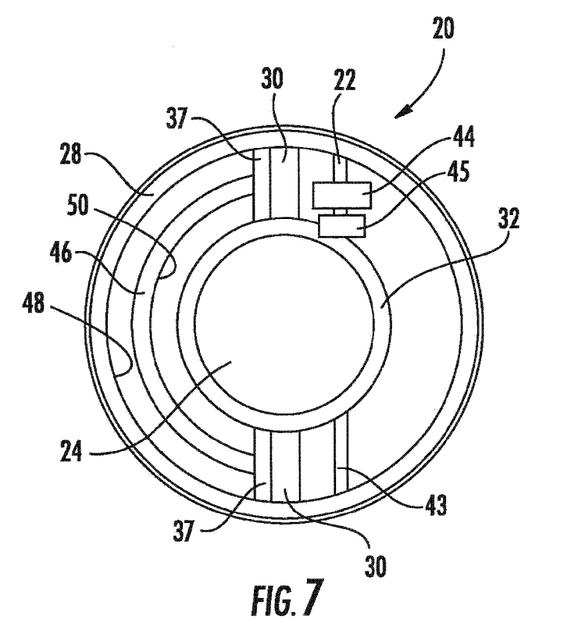
FIG. 7 is an end elevation view of the distal portion of the laparoscope as shown in FIG. 2.

As shown in FIGS. 2-4, the sphere 26 is configured to rotatably fit in the open distal end of the lens tube 22. Preferably, the diameter of the sphere 26 is only slightly less than the diameter of the lens tube 22 allowing for said rotation. A circular rubber lip 28 is fixed adjacent the distal end of the lens tube 22 surrounding the glass sphere 26. The rubber lip 28 tapers inwardly from a proximal surface to a distal surface. The sphere 26 and the rubber lip 28 are arranged in the lens tube 22 such that the rubber lip contacts the sphere 26 while still allowing the sphere 26 to rotate relative to the lens tube 22. This arrangement allows the rubber lip 28 to serve as a seal between the distal end of the lens tube 22 and the sphere 26. The rubber lip 28 also functions as a barrier for large debris that may adhere to the glass sphere 26 during use. Specifically, as the sphere 26 rotates, any debris will contact the rubber lip 28 and fall into the operating field preventing the debris from entering the lens tube 22.

The sphere 26 defines holes 27 at opposite poles of the sphere. Opposed lens posts 30 extend inwardly from the inner surface of the lens tube 22. The lens posts 30 pass through the holes 27 in the sphere 26 and extend inwardly where the posts 30 support a lens holder 32. The lens 24 is mounted in the lens holder 32 at the center of the sphere 26. The lens posts 30 also function to hold the sphere 26 in the lens tube 22 such that a portion of the sphere is housed within the lens tube 22 and the remainder of the sphere 26 extends from the distal end of the lens tube 22. The sphere 26 rotates on an axis extending through the lens posts 30.

An optic channel 34 extends from the sphere 26 to the optics of the camera at the proximal end of the laparoscope 20. The optic channel 34 is defined by a hollow cylindrical wall 36. The distal end of the wall 36 is positioned immediately adjacent the sphere 26. The optic channel wall 36 is supported by opposed longitudinally extending channel posts 37 and preferably runs the entire length of the body 21 of the laparoscope 20, approximately 440 mm. The inner diameter of the wall 36 is less than the diameter of the sphere 26 such that a portion of the sphere 26 extends into the open distal end of the optic channel 34. The end of the optic channel wall 36 is curved for closely accommodating the surface of the sphere 26 without contact. The optic channel wall 36 is aligned with the optical axis of the lens. In one embodiment, the optical axis of the lens 24 is further aligned with the longitudinal axis of the lens tube 22. The inside diameter of the optic channel wall 36 and the lens holder 32 are the same or substantially the same to ensure that there are no optical aberrations. In this arrangement, any light that enters the lens 24 will be transmitted through the optic channel 34 wherein the optic channel wall 36 serves as a boundary of the optic path. Since the glass sphere 26 has a low refractive index, rotation of the sphere 26 will not significantly refract the incoming light and deteriorate the image.

A drivable gear mechanism 40 is supported in the lens tube 22 by a opposed posts 42, 43 extending between the inner surface of the lens tube 22 and the optic channel wall 36. While the dimensions of the gear mechanism 40 can vary, the gear mechanism 40 should be sufficiently miniature such that gear mechanism 40 will not affect the functional features of the laparoscope 20. The gear mechanism 40 is positioned by the posts 42 relative to the optic channel wall 28. The longer gear post 43 further supports and secures the distal end of the optic channel wall 36 to the lens tube 22. The gear mechanism 40 is positioned so that a rubber gear 44 is in direct contact with the sphere 26 for rotating the sphere. The gear 44 may be coated with a rubberized material or other suitable coating that has sufficient traction with the glass sphere 26 for causing rotation without causing any mechanical changes to the glass sphere 26. The gear is powered for rotation by a motor 45 shown schematically in the FIGs. Electrical current is conveyed to the motor 45 over wires (not shown) extending through the body 21 of the laparoscope 20.

The optic channel posts 37, the outer surface of the optic channel wall 36, and the inner surface of the lens tube 22 between the optic channel posts 37 define a hemispherical longitudinal channel. The longitudinal channel is divided by a semi-circular channel partition 46 into an outer saline channel 48 and an inner vacuum channel 50 separated by the channel partition 46. The saline channel 48 is defined by the inner surface of the lens tube 22 and the outer surface of the channel partition 46. The vacuum channel 50 is defined by the inner surface of the channel partition 46 and the outer surface of the optic channel wall 36. The channel partition 44 runs the entire length of the laparoscope body 21 except for a small space located between the distal end of the partition wall 44 and the sphere 26. As described above, the optic channel wall 36 extends distally beyond the other channel walls and conforms to the sphere 26. The optic channel wall 36 is located directly behind the lens holding ring, which has the same inner and outer radius dimensions to provide a viewing channel which is similar to a normal laparoscope. The distal ends of the channels 48, 50 are shaped such that their walls fit against and engage the sphere 26, except for the middle wall, which is spaced from the sphere 26 to allow flow between the channels 48, 50.

The components of the laparoscope aside from the lens 24, the sphere 26, and the gear mechanism 40 may be made of a uniform stainless steel alloy. Alternatively, components of the laparoscope 20 may be made of a generally rigid plastic material, such as polycarbonate, but may be somewhat flexible so as to ease its insertion and manipulation.

Figure 10:
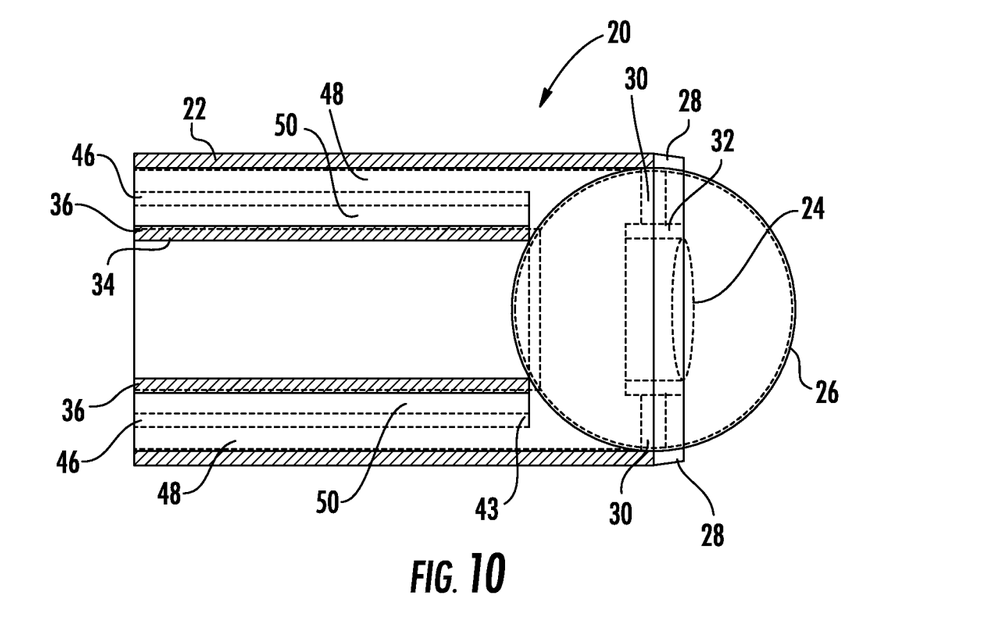
FIG. 10 is a longitudinal cross-section view of the distal portion of the laparoscope as shown in FIG. 9 with the laparoscope rotated 90°.

In use, a saline source (not shown) feeds saline into the saline channel 48. The saline should be a balanced saline solution or any other solution that is conventionally implemented in surgical procedures and provides minimal risk to the patient in the event of leaks. The saline contacts the sphere 26 at the outlet of the saline channel 48 causes the sphere 26 to rotate counter-clockwise as seen in FIG. 10. This rotational force works in conjunction with the gear mechanism 40. The wetted surface of the sphere 26 contacts the inner edge of the rubber lip 28 as the sphere rotates. This action simultaneously dries the sphere 26 and removes small debris so the debris does not escape back into the operating field. At the same time, the outer surface of the sphere 26 is wiped along its edges by the rubber wiper which removes solid debris from sphere as described above for preventing debris from entering the laparoscope. The surface of the sphere 26 is then rotated into the lens tube 22 where is it cleaned by the saline/vacuum system.

Figure 8:
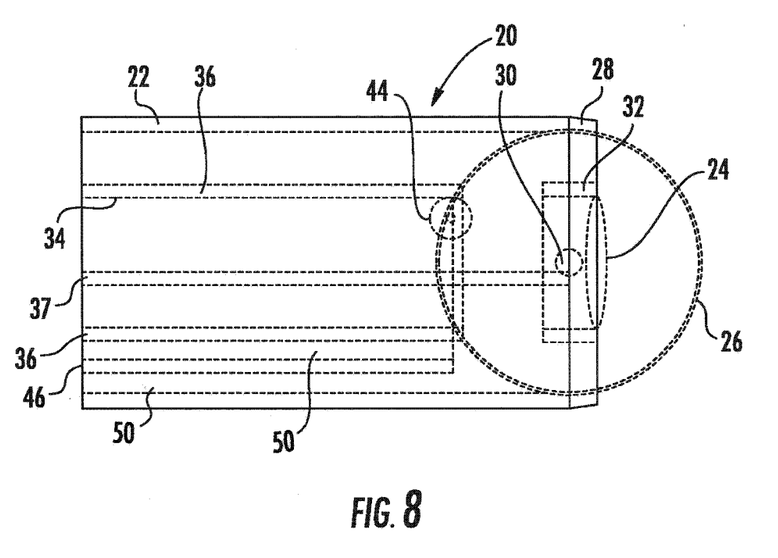
FIG. 8 is a side elevation view of the distal portion of the laparoscope as shown in FIG. 3 with the internal components shown in phantom.
Figure 9:
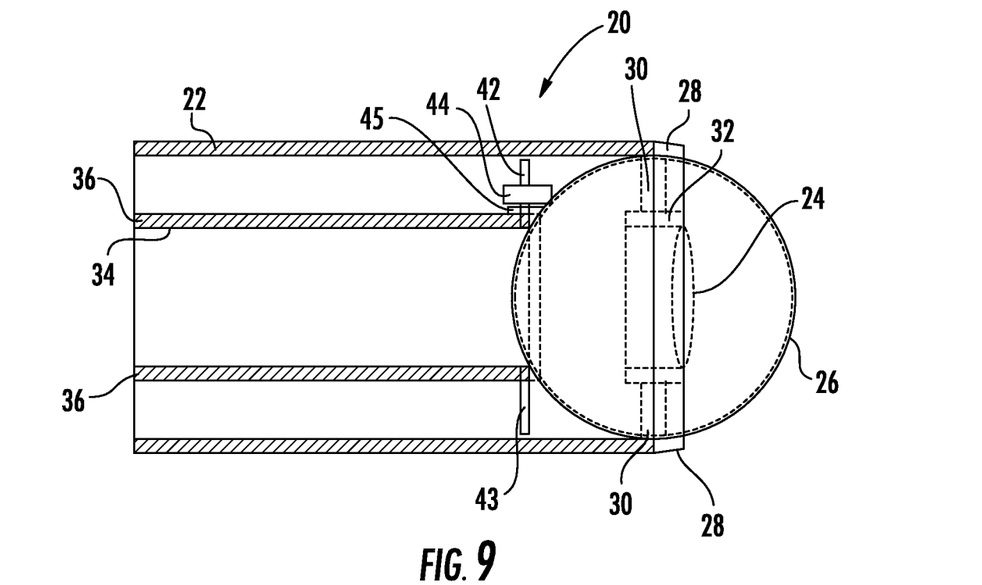
FIG. 9 is a longitudinal cross-section view of the distal portion of the laparoscope as shown in FIG. 3.

The vacuum channel 50 is powered by an external vacuum source (not shown). Residual saline and small debris removed from the sphere 26 are drawn into the vacuum channel 50. As depicted in FIGS. 8 and 10, the channel partition 46 is offset from the glass sphere 12. This arrangement allows saline used to clean and rotate the glass sphere 26. Debris and used saline is collected and removed by the vacuum channel 46 by negative pressure and the air flow serves to dry the surface of the sphere 26. Continuous airflow past the surface of the sphere 26 also minimizes debris deposit. This system of cleaning the sphere 26 maintains the visual clarity of the sphere 26 ensures that a clean and dry imaging surface is continually utilized during the surgical procedure. The lens 24 is completely encased inside the sphere 26 shielded from damage and contact by any debris or other foreign substances.

Cleaning of the surface of the sphere 26 with saline/vacuum system internal to the lens tube 22 provides a clear image of the operation field throughout surgery while using a conventional optical laparoscope. The device can be controlled by a physician using an external switch or button, which will power the gear, saline delivery, and vacuum, allowing the physician to control the mechanism.

The laparoscope as described herein has many advantages, including providing a means for maintaining a clear visual image of a surgical field during surgery. A laparoscope comprising the cleaning system can remain clean in the body throughout the surgery and does not need be removed from the patient for cleaning thereby minimizing interruptions to the surgical procedure. The cleaning occurs within the device so no waste is introduced into the patient which limits the potential for infection. Cleaning of the sphere may be continuous cleaning, or the physician may selectively power the cleaning system with touch of button for intermittent cleaning as needed. Further, by reducing the cleaning time associated with the laparoscopic camera, operating times as well as patient complications can be significantly reduced.

Although the laparoscope has been shown and described in considerable detail with respect to only a few exemplary embodiments thereof, it should be understood by those skilled in the art that we do not intend to limit the description to the embodiments since various modifications, omissions and additions may be made to the disclosed embodiments without materially departing from the novel teachings and advantages of the laparoscope, particularly in light of the foregoing teachings. For example, the lens tube and cleaning system as described and shown herein is applicable in any field that requires maintaining a clear imaging surface and adaptations of this device can be utilized for other visual fields. Accordingly, we intend to cover all such modifications, omission, additions and equivalents as may be included within the spirit and scope defined by the following claims. In the claims, means-plus-function clauses are intended to cover the structures described herein as performing the recited function and not only structural equivalents but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures.

We claim:

1. A laparoscope, comprising:
    an elongated insertion tube having an open distal end;
    optical means for conducting an optical image of a target, the optical means including an objective lens;
    a transparent sphere for housing the lens, the sphere rotatably disposed in the distal end of the tube such that a portion of the sphere protrudes from the tube;
    a ring-shaped wiper fixed to the distal end of the tube for circumferentially engaging the sphere;
    a wall extending the length of the interior of the tube for defining a pair of channels opening proximal and adjacent to the sphere; and
    means disposed in the tube for rotating the sphere while the lens remains stationary, wherein the wiper removes debris and fluids from the surface of the sphere as the sphere rotates.

2. The laparoscope as recited in claim 1, further comprising a saline source for delivering saline to the sphere via one of the pair of channels.

3. The laparoscope as recited in claim 2, further comprising a vacuum source for drawing vacuum to the sphere for recovering used saline and other materials from proximal the surface of the sphere.

4. The laparoscope as recited in claim 1, wherein the rotating means comprises a gear mechanism supported in the interior of the tube, the gear mechanism including
    a gear configured for operatively engaging the sphere for rotating the sphere, and
    a motor for rotating the gear and the sphere.

5. The laparoscope as recited in claim 4, wherein the gear comprises a rubberized surface for providing traction with the glass sphere for causing rotation of the sphere with the gear.

* * * * *